United States Patent [19]

Seto et al.

[11] Patent Number: 5,876,669

[45] Date of Patent: Mar. 2, 1999

[54] BIOCHEMICAL ANALYSIS APPARATUS AND INCUBATOR FOR THE SAME

[75] Inventors: Yoshihiro Seto; Fumio Sugaya, both of Kanagawa-ken; Takaki Arai, Saitama-ken, all of Japan

[73] Assignee: Fuji Photo Film Co., Ltd., Kanagawa-ken, Japan

[21] Appl. No.: 26,399

[22] Filed: Feb. 19, 1998

Related U.S. Application Data

[62] Division of Ser. No. 676,633, Jul. 10, 1996, Pat. No. 5,753,184, which is a division of Ser. No. 277,422, Jul. 18, 1994, Pat. No. 5,560,888.

[30] Foreign Application Priority Data

| Jul. 16, 1993 | [JP] | Japan | 5-177058 |
| Sep. 14, 1993 | [JP] | Japan | 5-228412 |
| Jul. 11, 1994 | [JP] | Japan | 6-158329 |

[51] Int. Cl.⁶ .................................................. G01N 35/10
[52] U.S. Cl. ............................... 422/64; 422/63; 422/66; 436/43; 436/46
[58] Field of Search ................................ 422/63, 64, 65, 422/66, 104; 436/43, 44, 46, 48

[56] References Cited

U.S. PATENT DOCUMENTS

| 4,296,069 | 10/1981 | Smith et al. | 422/64 |
| 4,298,571 | 11/1981 | DiFulvio et al. | 422/65 |
| 4,568,519 | 2/1986 | Hamilton et al. | 422/64 |
| 4,584,275 | 4/1986 | Okano et al. | 436/46 |
| 4,857,471 | 8/1989 | Salzman et al. | 436/43 |
| 4,963,333 | 10/1990 | Shaw et al. | 422/99 |
| 5,034,191 | 7/1991 | Porte | 436/46 |
| 5,037,613 | 8/1991 | Shaw et al. | 422/64 |
| 5,075,079 | 12/1991 | Kerr et al. | 422/64 |
| 5,102,624 | 4/1992 | Muraishi | 422/64 |
| 5,106,586 | 4/1992 | Muszak et al. | 422/99 |
| 5,174,960 | 12/1992 | Shaw et al. | 422/63 |
| 5,266,267 | 11/1993 | Albano et al. | 436/46 |
| 5,330,716 | 7/1994 | Shaw et al. | 422/63 |
| 5,447,690 | 9/1995 | Sugaya | 422/64 |

FOREIGN PATENT DOCUMENTS

| 0397256 | 11/1990 | European Pat. Off. . |
| 0458138 | 11/1991 | European Pat. Off. . |
| 0634657 | 1/1995 | European Pat. Off. . |
| 0634659 | 1/1995 | European Pat. Off. . |

*Primary Examiner*—Long V. Le
*Attorney, Agent, or Firm*—Sughrue, Mion, Zinn, Macpeak & Seas, PLLC

[57] ABSTRACT

In a biochemical analysis apparatus, a dry-type frameless chemical analysis film having a base and a reagent layer formed thereon is taken out from a cartridge in which a plurality of such frameless chemical analysis films are stacked. Then the film is spotted with a sample liquid and is transferred to a cell in an incubator to be incubated at a constant temperature, whereby coloring reaction between the reagent layer and a particular biochemical component in the sample liquid is caused and the optical density of the coloring matter formed is measured. A horseshoe-like film transfer member receives the film taken out from the cartridge and inserts it into the cell while holding it, and a suction member enters the cell from below the cell and holds the film inserted by the film transfer member.

4 Claims, 10 Drawing Sheets

F I G. 15
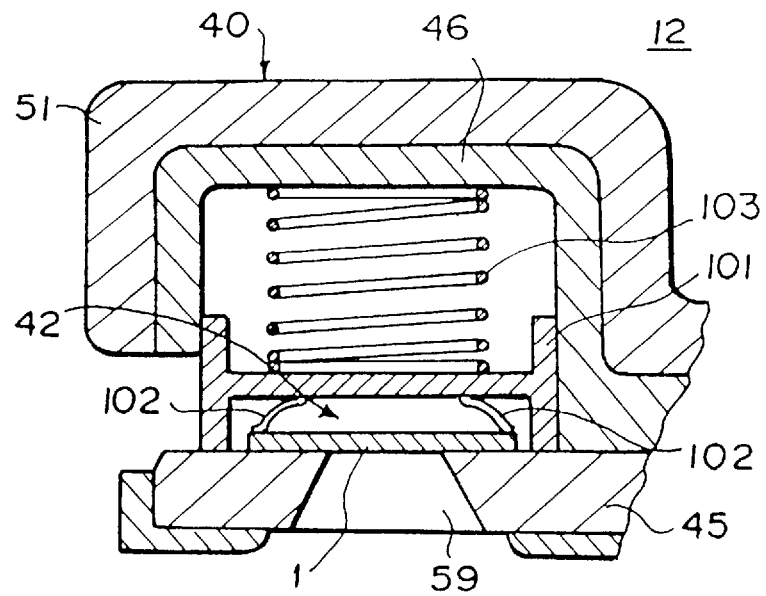
F I G. 16
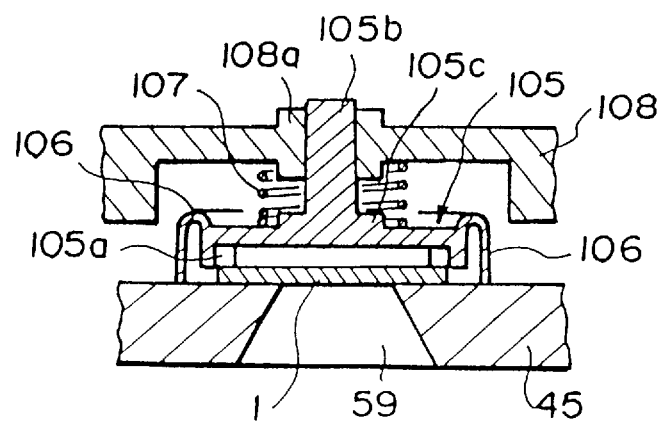

BIOCHEMICAL ANALYSIS APPARATUS AND INCUBATOR FOR THE SAME

This is a Divisional of application Ser. No. 08/676,633 filed Jul. 10, 1996 now U.S. Pat. No. 5,753,184 which is a Divisional of application Ser. No. 08/277,422 filed Jul. 18, 1994 now U.S. Pat. No. 5,560,888.

BACKGROUND OF THE INVENTION

1. Field of the Invention

This invention relates to a biochemical analysis apparatus which spots a sample liquid such as blood, serum, urine or the like on a dry-type frameless chemical analysis film having thereon a reagent layer (spreading layer) whose optical density changes by chemical reaction, immunoreaction, or the like with a specific biochemical component contained in the sample liquid and determines the concentration of the specific biochemical component in the sample liquid by measuring the optical density of the film.

2. Description of the Prior Art

There has been put into practice a biochemical analysis apparatus using a dry-type chemical analysis film with which a specific component contained in a sample liquid can be quantified through a droplet of the sample liquid spotted on the slide. When chemical components or the like contained in a sample liquid is analyzed using such a dry-type chemical analysis film, a droplet of the sample liquid is spotted on the slide and is held at a constant temperature for a predetermined time (incubation) in an incubator so that coloring reaction occurs, and the optical density of the color formed by the coloring reaction is optically measured. That is, measuring light containing a wavelength which is preselected according to the combination of the component to be analyzed and the reagent contained in the reagent layer of the film is projected onto the film and the optical density of the film is measured. Then the component to be analyzed is quantified on the basis of the optical density using a calibration curve which represents the relation between the concentration of the biochemical component and the optical density.

The chemical analysis film is generally composed of a base film of plastic or the like and a reagent layer and a spreading layer formed on the base film and is conventionally generally provided with a plastic frame which holds the chemical analysis film flat which is apt to warp into a roof tile shape when it dries.

The chemical analysis films are transferred to an incubator one by one after spotted with a sample liquid. Transfer of the chemical analysis slides can be done, for instance, by a reciprocating claw member as disclosed in U.S. Pat. Nos. 4,296,069 and 4,568,519 and the like. The frame facilitates transfer of the chemical analysis film.

However, the frame increases the volume of the chemical analysis film and results in increase in the size of various parts handling the film such as cells in the incubator for incubating the chemical analysis films. Thus the frame of the chemical analysis film is obstructive to reducing the size of the biochemical analysis apparatus and at the same time reduces the film accommodating capacity of the incubator, which obstructs increase in handling capability of the overall biochemical analysis apparatus.

An attempt to use a dry-type chemical analysis film without frame (will be referred to as "frameless chemical analysis film", hereinbelow) will encounter the following difficulties. That is, in order to automate the analysis, the frameless chemical analysis film must be surely transferred to the incubator and incubated therein. Though the frameless chemical analysis film is apt to warp into a roof tile shape when it dries as described above and the curvature of the warp changes in response to spotting of the sample liquid, the sample liquid must be precisely spotted on the curled frameless chemical analysis film and the film must be transferred to the incubator without touching the sample liquid thereon and the optical density must be measured with the film held flat and tightly enclosed.

That is, when the optical density is measured with some films curled and some films flat, measuring errors are produced. Further increase in temperature during heating differs and progressing rate of coloring reaction varies according to the curvature of the chemical analysis film, which can result in measuring errors. Accordingly, measurement of the optical density must be effected with the films held flat in the incubator. Further when a part of the film transfer means is in contact with the sample liquid during transfer of the films spotted with the sample liquid, the sample liquid adhering to the film transfer means can contaminate the reagent layer on the next chemical analysis film and adversely affect the accuracy of the analysis.

Further when the film transfer means is arranged to hold the film under suction on the bottom side (the side opposite to the reagent layer) and to insert the film into cell in the incubator, the incubator must be provided with a passage through which the suction member goes in the incubator, which makes it difficult to seal the film in the cell during incubation. When the film is not tightly enclosed, the sample liquid can evaporate and the vapor can contaminate other sample liquid, which can adversely affect the accuracy of the analysis.

Further when a transfer mechanism for taking out the chemical analysis slide or the frameless chemical analysis film from a film supplier and transferring it to the incubator (during the transfer, a sample liquid is spotted on the film or the slide) is provided between the film supplier and the incubator to transfer the film or the slide along a linear path, the space between the supplier and the incubator must be large, which increases the overall size of the chemical analysis apparatus.

SUMMARY OF THE INVENTION

In view of the foregoing observations and description, the primary object of the present invention is to provide an biochemical analysis apparatus in which the frameless chemical analysis film can be transferred to an incubator without being contaminated and can be incubated in a tightly enclosed state.

Another object of the present invention is to provide an biochemical analysis apparatus in which the space between the film supplier and the incubator can be small and the transfer mechanism for taking out the frameless chemical analysis film from the film supplier and transferring it to the incubator can be compact in size.

Still another object of the present invention is to provide an incubator which is useful to such a biochemical analysis apparatus.

In accordance with one aspect of the present invention, there is provided a biochemical analysis apparatus in which a dry-type frameless chemical analysis film having a base and a reagent layer formed thereon is taken out from a cartridge in which a plurality of such frameless chemical analysis films are stacked, is spotted with a sample liquid and is transferred to an incubator to be incubated at a constant temperature, and the concentration of a biochemical component in the sample liquid is measured through a chemical reaction between the reagent layer and the biochemical component, and which is characterized by having a cell formed in the incubator into which the chemical analysis film is inserted, a film transfer means which receives the film taken out from the cartridge and holds the film to insert it into the cell, and a holding means which enters the cell from below the cell and holds the film inserted into the cell of the incubator by the film transfer means while the film is being held by the film transfer means.

Preferably said film transfer means comprises a film transfer member which is substantially like a horseshoe in shape and attracts the frameless chemical analysis film on the upper surface thereof to hold it under a suction force, and said holding means comprises a suction member which is moved up and down into and away from the cell through a light measuring window which opens at the bottom of the cell of the incubator.

Further it is preferred that said incubator is provided with a fixing means which fixes the frameless chemical analysis film held by the holding means on the bottom of the cell after the film insertion means is retracted from the cell.

Preferably the fixing means has a film retainer which presses the frameless chemical analysis film against the bottom of the cell only at corners of the film.

Further it is preferred that the bottom of the cell in the incubator be formed by a substrate which has a flat upper surface and is provided with a plurality of light measuring windows at predetermined intervals.

In the biochemical analysis apparatus with the arrangement described above, the frameless chemical analysis film taken out from the cartridge is received by the film transfer means with the reagent layer facing upward and the sample liquid is spotted on the reagent layer. Then the film 1 spotted with the sample liquid is inserted into the cell in the incubator by the film transfer means and the film transfer means retracts from the cell after transferring the film to the holding means. Thereafter the holding means sets the film in a predetermined position in the cell and then retracts from the cell leaving the film there. In the cell, the film is incubated in a tightly enclosed state and the coloring reaction is measured through the light measuring window in the bottom of the cell.

In this manner, the frameless chemical analysis film can be inserted into the incubator and incubated therein and measurement can be effected without deteriorating the measuring accuracy. Thus in accordance with the present invention, chemical analysis film without frame can be used, which results in miniaturization of various parts of the biochemical analysis apparatus and in reduction of the analyzing cost.

Further when the film transfer means comprises a horseshoe-like film transfer member and the holding means comprises a suction member which is moved up and down into and away from the cell through the light measuring window, the dry-type frameless chemical analysis film can be transferred with a simple structure. Further when the incubator is provided with a securing means which secures the film on the incubator, incubation of the film can be surely effected. Especially when the securing means holds down the film only at the corners thereof, the sample liquid on the film cannot contaminate the securing means. Further when the bottom of the cell is flat, cleaning of the cell is facilitated.

In accordance with another aspect of the present invention, there is provided a biochemical analysis apparatus in which a cartridge for storing a stack of a plurality of a dry-type frameless chemical analysis films each having a base and a reagent layer formed thereon is housed in a film supplier, and the dry-type frameless chemical analysis film is taken out from the cartridge, is spotted with a sample liquid and is transferred to an incubator to be incubated at a constant temperature, and the concentration of a biochemical component in the sample liquid is measured through a chemical reaction between the reagent layer and the biochemical component, wherein the apparatus characterized by having a film takeout means which takes out the frameless chemical analysis film from the cartridge in the film supplier and conveys the film in a first direction and a film transfer means which receives the film from the film takeout means and conveys the film in a second direction into the incubator, the first and second directions being at an angle with respect to each other.

Preferably the first and second directions are at right angles with each other.

Preferably the sample liquid is spotted on the frameless chemical analysis film at the intersection of the first and second directions or in a position near the intersection.

Further preferably the film takeout means is in the form of a suction means and the film transfer means is in the form of a horseshoe-like film transfer member.

When the first and second directions are at an angle with each other, i.e., when the first and second directions are not in alignment with each other, the transfer mechanism including the film takeout means and the film transfer means need not be in alignment with the film supplier and the incubator, and accordingly, the film supplier and the incubator can be positioned close to each other, whereby the chemical analysis apparatus can be small in the overall size.

When the sample liquid is spotted on the frameless chemical analysis film at the intersection of the first and second directions or in a position near the intersection, the mechanism for spotting the sample liquid on the frameless chemical analysis film can easily positioned not to interfere with the film supplier or the incubator, whereby layout of the respective means is facilitated. Further when the film takeout means is in the form of a suction means and the film insertion means is in the form of a horseshoe-like film transfer member, the direction of conveyance of the frameless chemical analysis film can be easily changed by a right angle without rotating the film, whereby the film can be transferred from the film takeout means to the film insertion means with a simple structure.

In accordance with still another aspect of the present invention, there is provided an incubator for incubating at a constant temperature a dry-type frameless chemical analysis film which has a base and a reagent layer formed thereon and has been spotted with a sample liquid and is characterized by having a cell into which the frameless chemical analysis film can be inserted, a pressing means which presses the inserted frameless chemical analysis film against the bottom of the cell and an enclosing means which tightly encloses a space in which the frameless chemical analysis film is accommodated.

Preferably said pressing means presses the frameless chemical analysis film at an area where the sample liquid spotted on the film does not spread out. Further it is preferred that said pressing means and the enclosing means be movable relative to each other.

Further it is preferred that said pressing means be formed by a film retainer which is urged by a first urging means in the direction in which the film retainer presses the inserted frameless chemical analysis film against the bottom of the cell, and said enclosing means be formed by a cell cover which is urged by a second urging means in the direction in which the cell cover tightly encloses the frameless chemical analysis film pressed by the film retainer, at least one of the first and second urging means being disposed outside the cell cover. The pressing and the enclosing means may be formed integrally with each other and urged by a single urging means.

In the incubator described above, the frameless chemical analysis film can be incubated in a flat state by virtue of the pressing means which presses the film against the bottom of the cell and in a tightly enclosed state by virtue of the enclosing means and the coloring reaction on the film can be measured through, for instance, a light measuring window in the bottom of the cell.

In this manner, the frameless chemical film can analysis film can be incubated in a flat and tightly enclosed state and measurement can be effected without deteriorating the measuring accuracy. Thus in accordance with the present invention, chemical analysis film without frame can be used, which results in miniaturization of various parts of the biochemical analysis apparatus and in reduction of the analyzing cost.

Further when the pressing means presses the frameless chemical analysis film at an area where the sample liquid spotted on the film does not spread out, the pressing means can be prevented from being contaminated with the sample liquid. Further when said pressing means and the enclosing means be movable relative to each other, the frameless chemical analysis film can be surely enclosed even if the thickness of the film varies. Further when the first and/or second urging means is disposed outside the cell cover, the inner space of the cell cover can be smaller in volume and the cell cover has a smaller inner surface area, whereby vaporization of the sample liquid can be suppressed and the concentration of reaction gases can be made constant to stabilize the reaction, and at the same time the amount of gas to be adsorbed by the wall of the cell cover can be reduced. Further when the pressing means and the enclosing means are formed integrally with each other and urged by a single urging means, the structure is simplified.

BRIEF DESCRIPTION OF THE DRAWINGS

FIG. 15 is a fragmentary cross-sectional view showing another modification of the incubator, and FIG. 16 is a fragmentary cross-sectional view showing still another modification of the incubator.

DESCRIPTION OF THE PREFERRED EMBODIMENT

Figure 1:
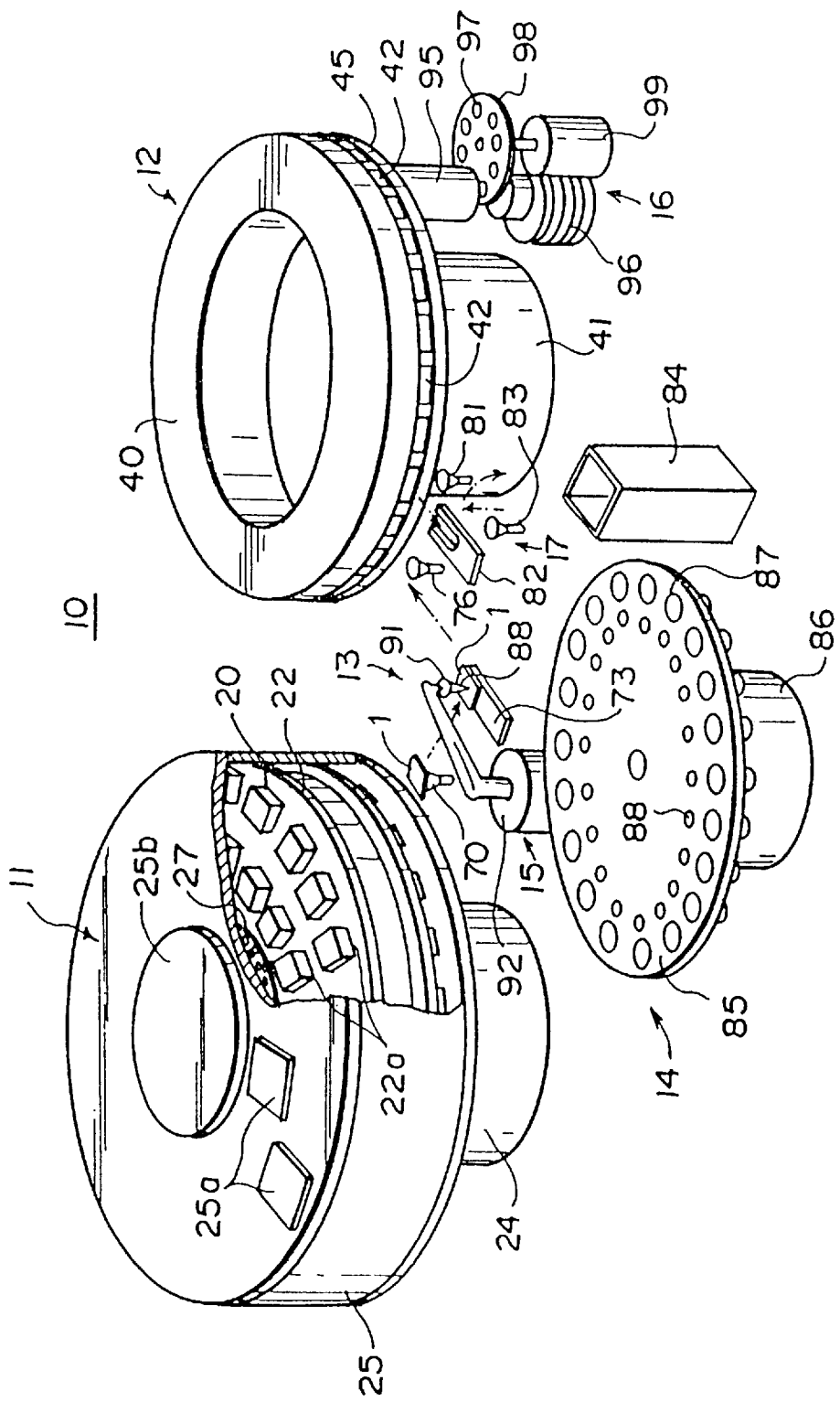
FIG. 1 is a perspective view showing a biochemical analysis apparatus in accordance with an embodiment of the present invention.

In FIG. 1, a biochemical analysis apparatus 10 in accordance with an embodiment of the present invention comprises a film supplier 11 in which a plurality of rectangular dry-type frameless chemical analysis films 1 are stored, an incubator 12 which is disposed beside the film supplier 11 and incubates the frameless chemical analysis films 1 transferred from the film supplier 11, a film transfer means 13 which transfers the frameless chemical analysis films 1 from the film supplier 11 to the incubator 12, a sample liquid supplier 14 in which a plurality of sample liquids such as serum, urine or the like are stored, a spotting mechanism 15 which spots one of the sample liquids in the sample liquid supplier 14 on the frameless chemical analysis film 1 on the way to the incubator 12, and a light measuring system 16 disposed below the incubator 12.

Figure 2:
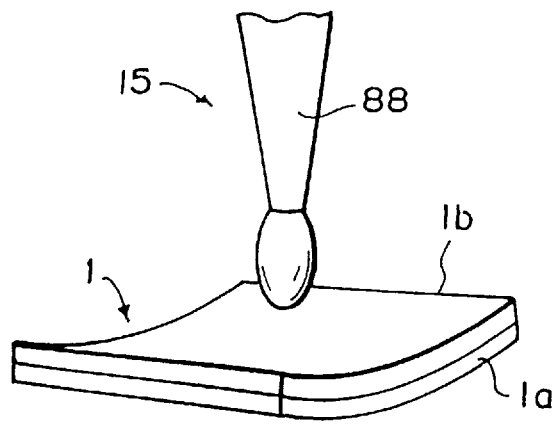
FIG. 2 is a perspective view showing spotting of the sample liquid on the frameless chemical analysis film.

As shown in FIG. 2, the frameless chemical analysis film 1 comprises a light-transmissive base film 1a formed of plastic film such as polyethylene terephthalate and a reagent layer 1b (including a spreading layer) formed on the base film 1a. If necessary, a wear-resistant protective layer of fibrous material such as fabric may be formed on the reagent layer 1b. Such a protective layer may double as the spreading layer.

The dry-type frameless chemical analysis film 1 is apt to curl toward the reagent layer 1b in the dry state before spotting of the sample liquid, and the curvature varies depending on the dryness and the kind of the reagent layer 1b. The reagent layer 1b contains reagent (chemical analysis reagent or immunoassay reagent) which makes coloring reaction when it is mixed with a particular component in the sample liquid spotted by a nozzle tip 88 of the spotting mechanism 15 and is incubated at a constant temperature for a predetermined time. A plurality of kinds of frameless chemical analysis films 1 having different reagent layers 1b are prepared according to the terms of analysis, e.g., the chemical components or solid components to be analyzed in the sample liquids.

The frameless chemical analysis films 1 are stored in cartridges 20 (FIG. 3) for the respective terms of analysis. In the cartridge 20, a plurality of the frameless chemical analysis films 1 are stacked with the base films 1a facing downward. As shown in FIG. 1, the film supplier 11 is provided with a plurality of cartridge holding portions 22a which are arranged in inner and outer circles on a disk-like support 22 and a plurality of cartridges 20 loaded with the frameless chemical analysis films 1 are held in the respective cartridge holding portions 22a. The support 22 is supported for rotation on a base portion 24 and is rotated by a motor not shown so that a predetermined cartridge holding portion 22a is brought to a film takeout position where the film transfer means 13 takes out a frameless chemical analysis film 1 from the cartridge 20.

The support 22 is provided with a cover 25 which encloses inner space of the film supplier 11. The cover 25 is provided with a pair of openings 25a provided with lids and the cartridges 20 can be taken out and inserted into the cartridge holding portion 22a through the openings 25a. An dehumidifying agent holding portion 27 is formed in the support 22 at the center thereof and dehumidifying agent is loaded in the dehumidifying agent holding portion 27 through an opening 25b formed in the cover 25. The opening 25b is provided with a lid. Thus the inner space of the film supplier 11 is kept dry.

A film takeout port (not shown) is provided in the lower surface of the cover 25 in the film takeout position and a shutter is provided to open and close the film takeout port. The shutter is opened when the frameless chemical analysis film 1 is taken out from the cartridge 20 and a suction pad 70 of the film transfer means 13 is inserted into the film supplier 11 through the shutter and takes out the lowermost film 1 in the cartridge 20.

The cartridges 20 are loaded in the support 22 so that their film takeout openings 20a (FIG. 3) are faced toward the center of the support 22 and the film takeout port is elongated in the radial direction of the support 22. The suction pad 70 inserted into the film supplier 11 through the film takeout port is further inserted into the cartridge 20 through an opening in the bottom of the cartridge 20 to attract the lowermost film 1 in the cartridge 20 under a suction force and is moved toward the center of the support 22 to take out the lowermost film 1 from the cartridge 20.

The incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The frameless chemical analysis films 1 are incubated in the cells 42.

As shown in more detail in FIGS. 4 to 8, the body portion 40 comprises a lower disk 45 having a flat upper surface and an upper disk 46 provided on the lower disk 45 and is fixed to the lower disk 45 by screws 47. The peripheral edge portion of the upper disk 46 is bulged upward to form an annular channel open downward. The lower edge of the outer peripheral edge of the upper disk 46 is spaced from the upper surface of the lower disk 45 to form an opening 42a which opens in the side surface of the incubator 12 and gives access to the cells 42. A heater 48 is disposed between the lower and upper disks 45 and 46 and the disks 45 and 46 are formed of material having high heat conductivity such as aluminum. The heater 48 is controlled to heat the frameless chemical analysis films 1 in the cells 42 to a predetermined temperature (e.g., 37° C.) on the basis of the output of a temperature sensor 49 (FIG. 5) disposed in the lower disk 45 near the cell 42. The outer surfaces of the lower and upper disks 45 and 46 are coated with thermal insulators 52 and 51.

The body portion 40 is supported by a bearing 50 provided on the lower surface of the lower disk 45 to be rotatable relative to a base 53. The lower disk 45 is provided with a central rotary shaft 45a and a gear 54 is fixedly mounted on the rotary shaft 45a. The gear 54 is in mesh with a drive gear 56 of a disk drive motor 55, whereby the body portion 40 of the incubator 12 is driven by the drive motor 55. A plurality of light measuring windows 59 are formed in the lower disk 45 to be opposed to the respective cells 42, and a cell cover 64 is provided above each of the light measuring windows 59 to tightly enclose the frameless chemical analysis film 1 positioned in the cell 42. A film retainer 61 for fixing the frameless chemical analysis film 1 in a predetermined position is provided in the cell cover 64. A measuring system 16 has a light measuring head 95 which is disposed below the body portion 40 in a light measuring position, and the body portion 40 is rotated to bring the light measuring window 59 of one of the cells 42 opposing to the light measuring head 95.

Figure 6:
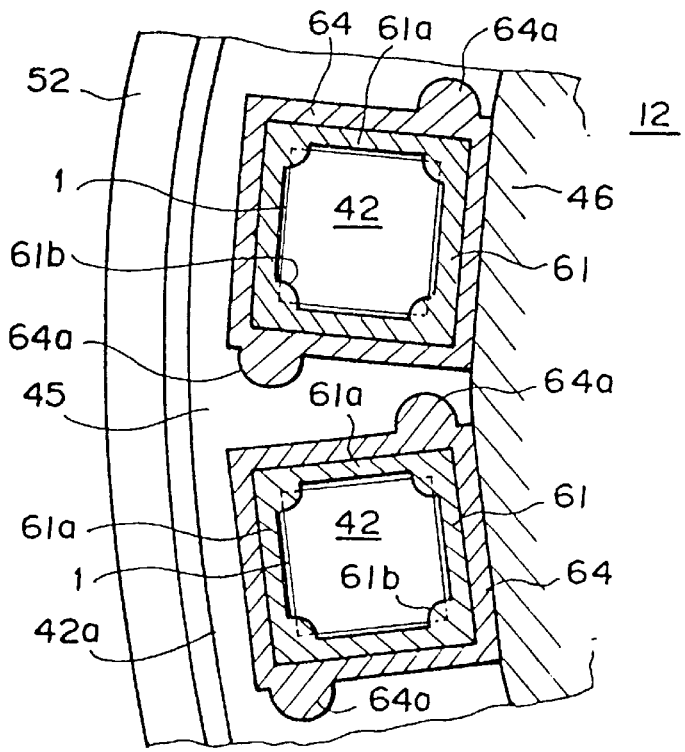
FIG. 6 is a cross-sectional view taken along line A—A in FIG. 5.
Figure 7:
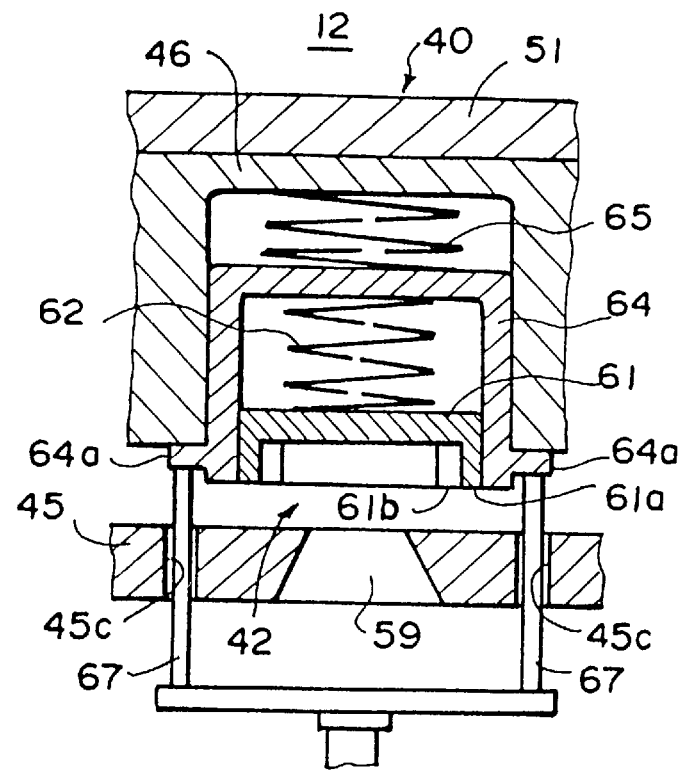
FIG. 7 is a fragmentary cross-sectional view of the incubator as seen in the radial direction of the incubator.
Figure 8:
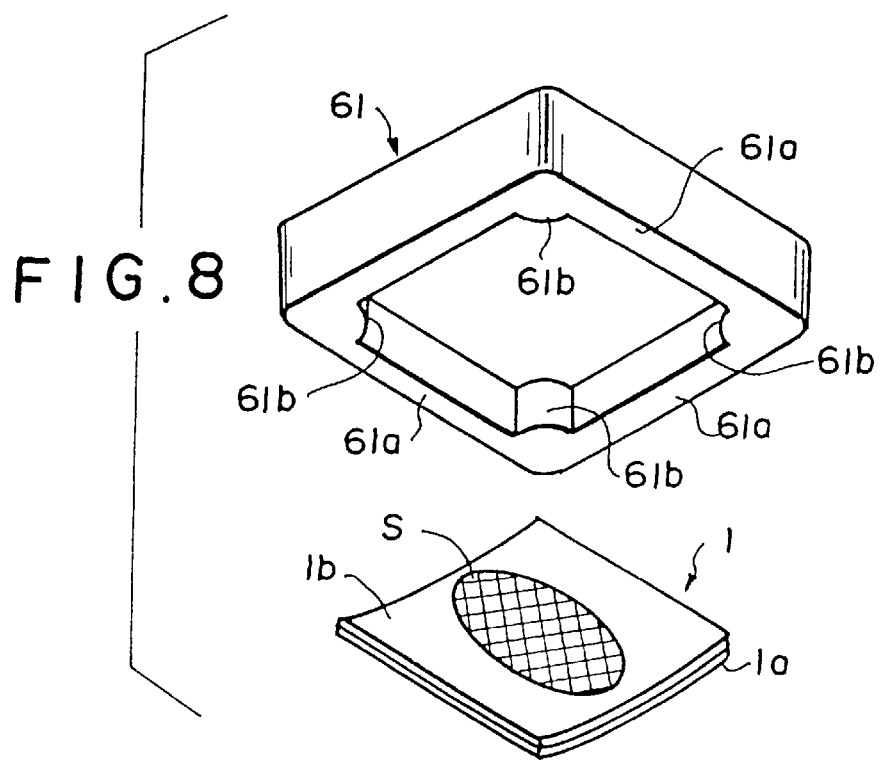
FIG. 8 is a perspective view showing the film retainer in relation to the frameless chemical analysis film spotted with the sample liquid.

The film retainer 61 has a rectangular frame portion 61a on the lower surface thereof as shown in FIGS. 6 and 8. The inner dimensions of the frame portion 61a is larger than the outer dimensions of the frameless chemical analysis film 1 and a protrusion 61b is provided at each corner of the frame portion 61a to project inward. When the film retainer 61 is moved downward against the film 1, only the protrusions 61b are brought into contact with the film 1 so that the retainer 61 is not brought into contact with the portion S (FIG. 8) over which the sample liquid can spread. The film retainer 61 is urged downward under the force of a spring provided on the upper surface of the retainer 61.

The cell cover 64 has a box-like body portion open downward and is positioned to surround the film retainer 61. The cell cover 64 is urged downward under the force of a spring 65 provided between the top wall of the cell cover 64 and the bottom of the channel in the upper disk 46. The lower surface of the cell cover 64 is pressed against the upper surface of the lower disk 45 to tightly enclose therein the frameless chemical analysis film 1. The spring 62 for urging downward the film retainer 61 is compressed between the upper surface of the film retainer 61 and the top wall of the cell cover 64, and the film retainer 61 is received in the cell cover 64 to be slidable relative to the cell cover 64 and to be movable up and down together with the cell cover 64.

The cell cover 64 and the film retainer 61 are formed of black polyethylene in order to suppress contamination due to adsorption of gases and influence of internal reflection of small amount of light transmitted through the film 1 on the light measurement.

A pair of engaging portions 64a (FIGS. 6 and 7) are formed on diagonally opposed corners of the lower portion of the cell cover 64 and a pair of through holes 45c are formed in the lower disk 45 to opposed to the engaging portions 64a. A pair of rods 67 are provided in a film insertion position and in a film takeout position. The rods 67 are moved upward through the holes 45c to abut against the engaging portions 64a of the cell cover 64 and lifts upward the cell cover 64 together with the film retainer 61 when the frameless chemical analysis film 1 is to be inserted into the cell 42 or taken out therfrom.

The film transfer means 13 for transferring the frameless chemical analysis film 1 from the film supplier 11 to the incubator 12 comprises said suction pad 70 which takes out the film 1 from the cartridge 20 and conveys it to a transfer position P in a first direction X (FIG. 12), a horseshoe-like film transfer member 73 which receives the film 1 held on the suction pad 70 from below the film 1 with the reagent layer 1b facing upward in the transfer position and conveys the film 1 in a second direction of Y perpendicular to the first direction X to insert the film 1 into the cell 42 in the incubator 12 through the opening 42a which opens sideways, and a suction member 76 which moves in and out the cell 42 from below the cell and receives the film 1 held by the film transfer member 73 inside the cell 42.

Figure 3:
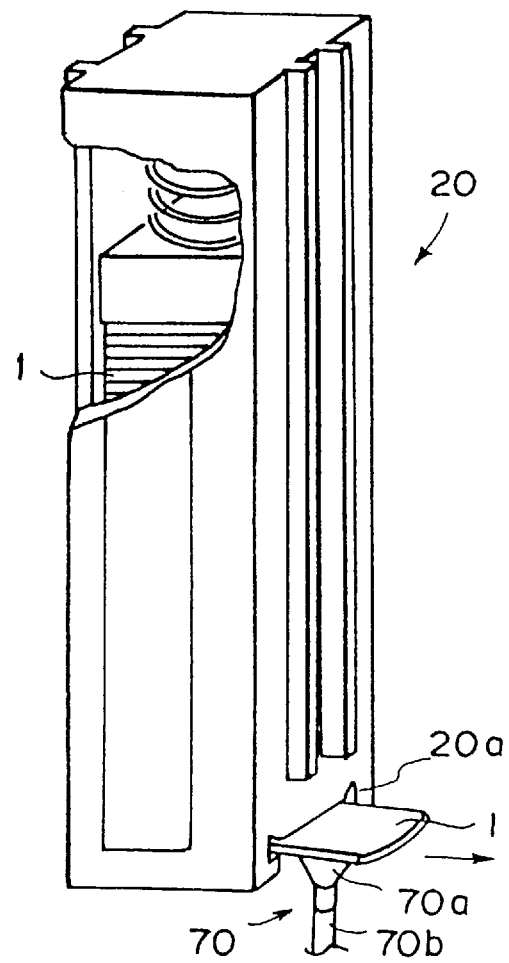
FIG. 3 is a perspective view showing the operation of taking out the frameless chemical analysis film from the cartridge.
Figure 4:
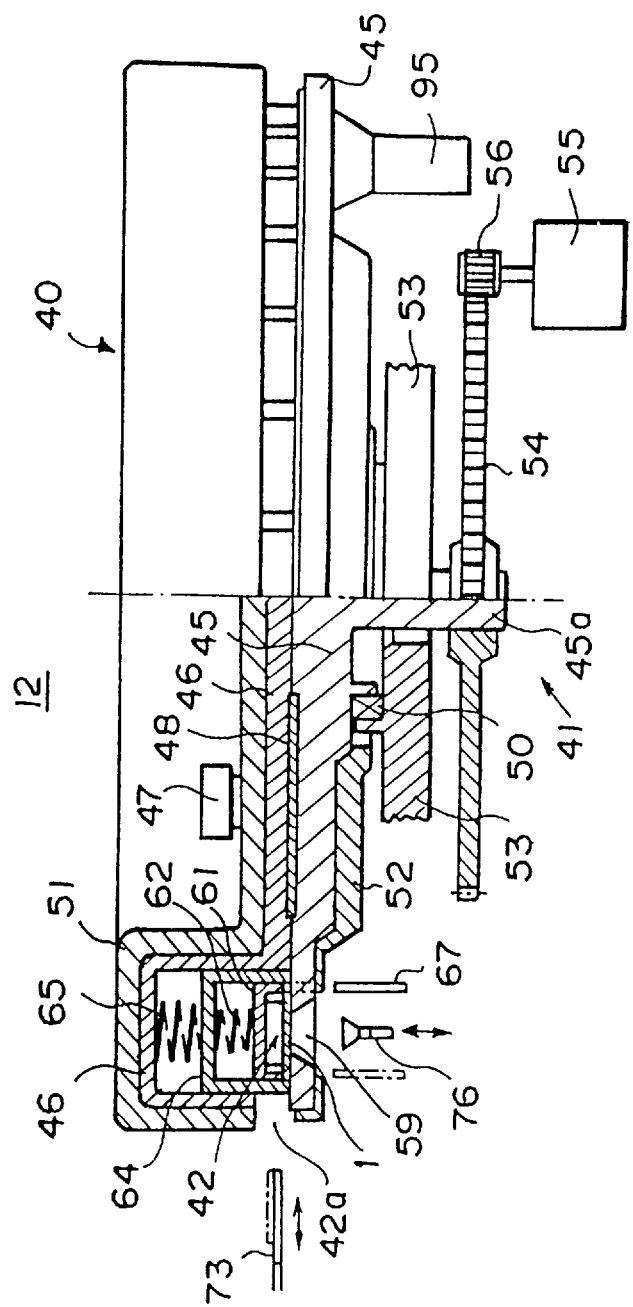
FIG. 4 is a front view partly in cross-section of the incubator.

As shown in FIG. 3, the suction pad 70 comprises a suction cup 70a which is directed upward and attracts the lower side of the base film 1a of the frameless chemical analysis film 1. The suction cup 70a is supported on a base portion 70b which is moved back and forth (away and toward the center of the support 22) and up and down by a drive mechanism (not shown) and is connected to a suction pump (not shown) through a vacuum tube.

The suction pad 70 is moved upward into the cartridge 20 through an opening in the bottom of the cartridge 20 and attracts the lowermost frameless chemical analysis film 1 on the base film side thereof. Then the suction pad 70 is slightly moved downward to curl the lowermost film 1 and then horizontally moved toward the center of the support 22 to take out the film 1 from the cartridge through an opening 20a in the side wall of the cartridge with the film 1 held in the curled state. Thereafter the suction pad 70 is moved downward outside the film supplier 11 through the film takeout port in the film supplier 11 and is moved away from the center of the support toward the position where the sample liquid is spotted on the film 1.

Figure 9:
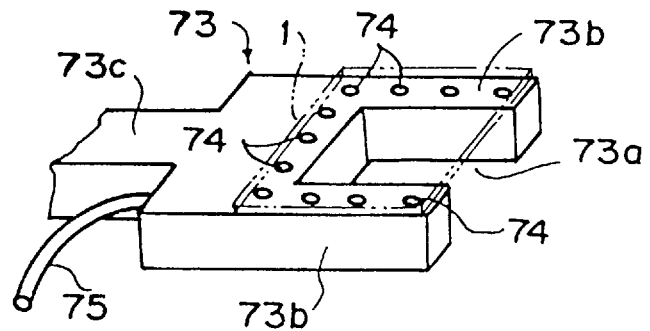
FIG. 9 is a fragmentary perspective view of the film transfer member.

As shown in FIG. 9, the film transfer member 73 is like a horseshoe in shape and has a flat upper surface. That is, the film transfer member 73 is bifurcated in the front end portion to form a pair of arm portions 73b extending on opposite sides of a cutaway portion 73a, and a plurality of suction holes 74 are formed to surround the cutaway portion 73a and to open in the upper surface of the film transfer member 73. The suction holes 74 are connected to a suction pump (not shown) through a vacuum tube 75. The base portion 73c of the film transfer member 73 is connected to a drive mechanism (not shown) to be inserted into the cell 42 in the incubator 12 through the opening 42a.

Figure 10A:
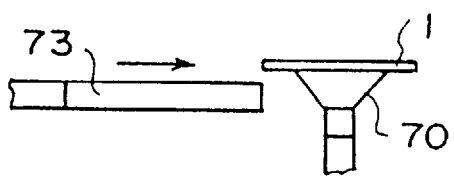
FIGS. 10A to 10C are schematic views for illustrating procedure for transferring the film from the suction pad to the film transfer member.
Figure 10B:
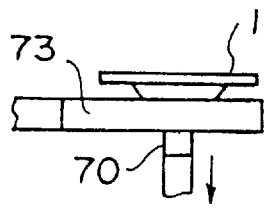
Figure 10C:
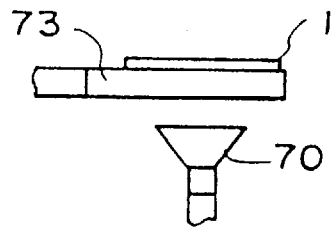

When the film transfer member 73 receives the film 1 from the suction pad 70, the film transfer member 73 is moved toward the suction pad 70 holding the film 1 as shown in FIG. 10A and is stopped in a position where the suction pad 70 is in the cutaway portion 73a of the film transfer member 73 with the film 1 positioned above the cutaway portion 73a as shown in FIG. 10B. Then the suction pad 70 is moved downward below the film transfer member 73 leaving the film 1 on the film transfer member 73 as shown in FIG. 10C. The film 1 left on the film transfer member 73 is held thereon under the suction force provided through the suction holes 74. When the position of the suction pad 70 relative to the film 1 held thereby is accurately controlled, the position of the film transfer member 73 relative to the film 1 can be accurately controlled and a predetermined amount of the sample liquid can be accurately spotted on the center of the reagent layer 1b of the frameless chemical analysis film 1 held by the film transfer member 73.

Figure 5:
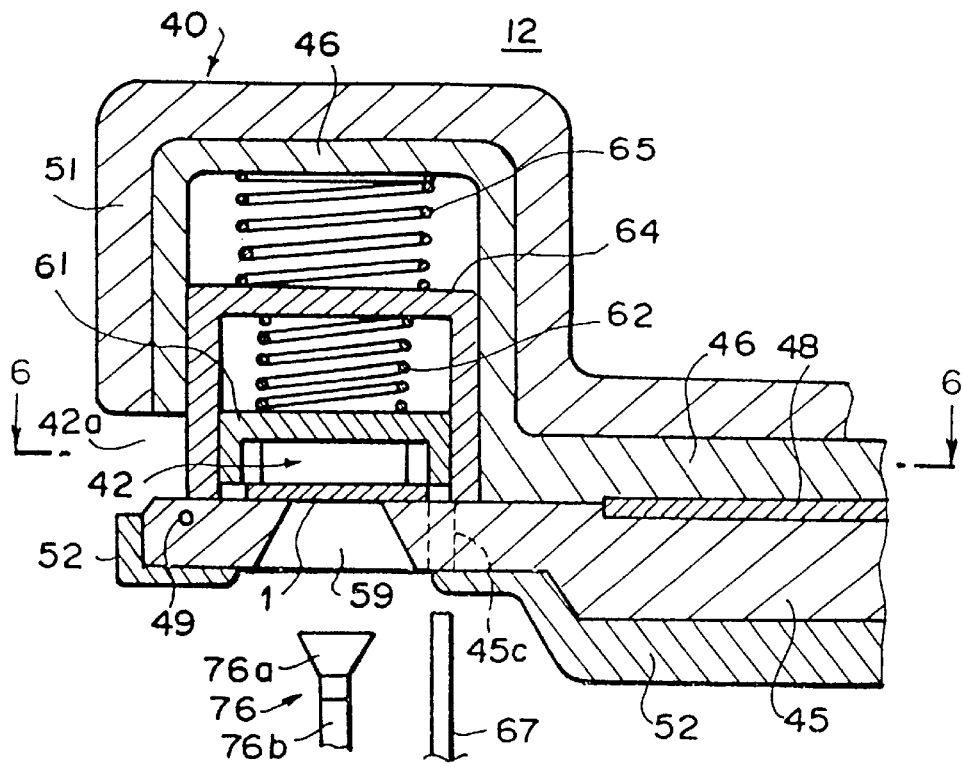
FIG. 5 is an enlarged fragmentary cross-sectional view showing the cell of the incubator.

As shown in FIG. 5, the suction member 76 is positioned below the cell 42 in the incubator 12 and comprises a suction cup 76a supported on a base portion 76b to be moved up and down by a drive mechanism not shown) into and away from the cell 42 through the light measuring window 59. The suction cup 76a is connected to a suction pump (not shown) through a vacuum hose.

A film removing means 17 (FIG. 1) is disposed in the film removing position of the incubator 12. The film removing means 17 comprises a removing suction pad 81 which attracts the film 1 in the cell 42 which has finished with measurement and lifts it, a horseshoe-like film removing member 82 which receives the film 1 from the removing suction pad 81 and transfers it outside the incubator 12 and a discarding suction pad 83 which receives the film 1 from the film removing member 82 and discards it into a discarding box 84.

The sample liquid supplier 14 comprises a turn table 85 which is rotated by a drive mechanism 86. The turn table 85 holds a plurality of sample tubes 87 filled with sample liquids which are arranged along the circumferential edge of the turn table 85 and is rotated to bring the sample tubes 87 to a sample liquid supplying position one by one. A plurality of nozzle tips 88 which are mounted on a spotting nozzle 91 to be described later are held on the turn table 85 inside the sample tubes 87.

The spotting means 15 for spotting the sample liquid on the frameless chemical analysis film 1 to be transferred to the incubator 12 comprises a spotting nozzle 91 which sucks and discharges the sample liquid, and a nozzle tip 88 is demountably mounted on the nozzle 91. The nozzle 91 is moved up and down and rotated by a drive mechanism 92. That is, the nozzle 91 sucks the sample liquid from the sample liquid supplier 14, is moved to the film 1 held by the film transfer member 73, and then spots the sample liquid on the film 1. The position where the sample liquid is spotted on the film 1 is a point on the path along which the film transfer member 73 is moved and is set at the intersection of the first and second directions X and Y in which the suction pad 70 and the film transfer member 73 are moved respectively or close to the intersection. The nozzle tip 88 is changed every time the sample liquid is changed.

The film 1 spotted with the sample liquid is transferred to the incubator 12 and incubated there. After incubation for a predetermined time, the optical density of the reagent layer 1b is measured by the light measuring system 16 (FIG. 1) disposed below the incubator 12. The light measuring system 16 comprises said light measuring head 95 for measuring the optical density of the color formed by the coloring reaction between the reagent layer 1b and the sample liquid. The light measuring head 95 projects measuring light containing light of a predetermined wavelength onto the reagent layer 1b through the base film 1a and detects reflected light with a photodetector. Light from a light source (lamp) 96 enters the light measuring head 95 through a filter 97 and is caused to impinge upon the reagent layer 1b by the head 95. A plurality of kinds of the filters 97 are mounted on a rotary disk 98 which is driven by an electric motor 99 and one of the filters 97 is selected according to the term of measurement.

The reflected light from the reagent layer 1b carries thereon optical information (more particularly the amount of light) on the amount of coloring matter formed by the coloring reaction between the reagent layer 1b and the sample liquid. The reflected light is received by the photodetector and the optical information carried by the reflected light is converted to an electric signal by the photodetector. The electric signal is input into a determination section through an amplifier. The determination section determines the optical density of the coloring matter formed by the coloring reaction between the reagent layer 1b and the sample liquid on the basis of the level of the electric signal and determines the concentration of a predetermined chemical component in the sample liquid.

The measurement by the biochemical analysis apparatus 10 is effected in the following manner. That is, a frameless chemical analysis film 1 is taken out by the suction pad 70 of the film transfer means 13 from a cartridge 20 storing therein frameless chemical analysis films 1 corresponding to the term of measurement. The film 1 held by the suction pad 70 is transferred to the film transfer member 73 with the reagent layer 1b facing upward and a sample liquid is spotted on the reagent layer 1b.

That is, a nozzle tip 88 is mounted on the spotting nozzle 91 of the spotting means 15 and the spotting nozzle 91 is moved above a desired sample tube 87 in the sample liquid supplier 14. Then the nozzle 91 is moved downward to bring the nozzle tip 88 into the sample liquid and the nozzle 91 sucks a predetermined amount of the sample liquid into the nozzle tip 88. Thereafter the nozzle 91 is moved above the center of the film 1 on the film transfer member 73 and moved downward toward the film 1, where a predetermined amount of sample liquid is spotted on the reagent layer 1b from the nozzle tip 88. The sample liquid spreads over the reagent layer 1b and mixes with the reagent therein.

Figure 11A:
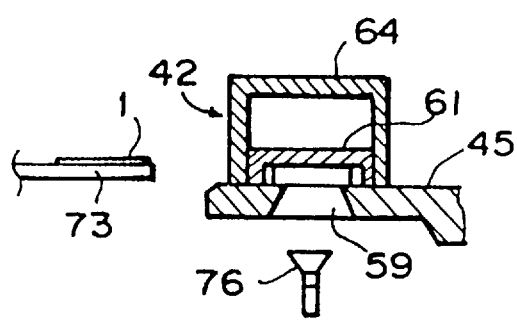
FIGS. 11A to 11G are schematic views for illustrating procedure for inserting the film into the incubator.
Figure 11E:
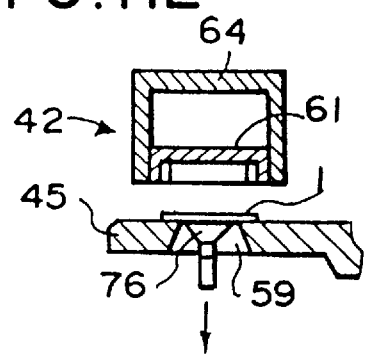
Figure 11B:
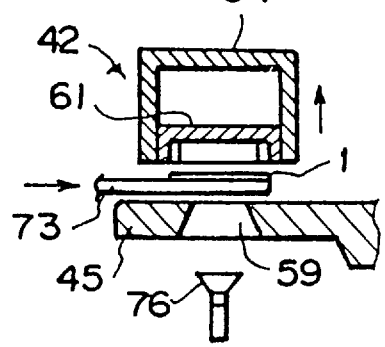
Figure 11F:
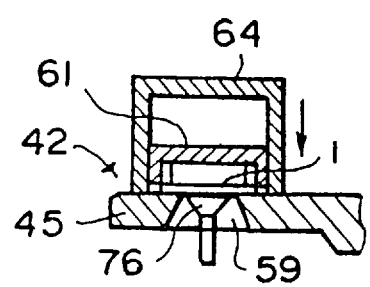
Figure 11C:
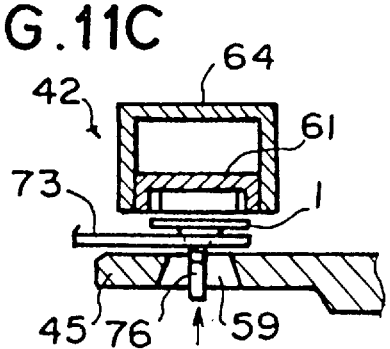
Figure 11G:
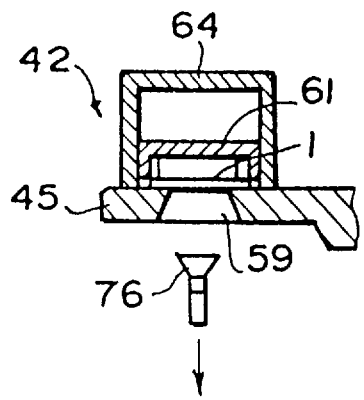
Figure 11D:
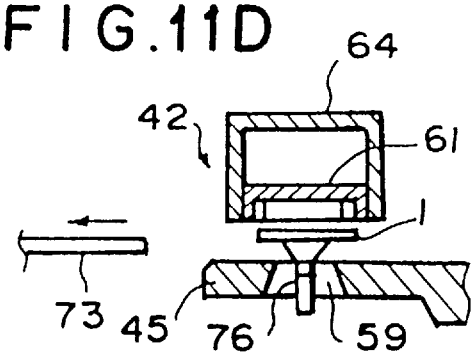

The film 1 spotted with the sample liquid is inserted into one of the cells 42 of the incubator 12 through the opening 42a by the film transfer member 73. When the film 1 is inserted into the cell 42, the incubator 12 is first rotated to bring a vacant cell 42 to the film insertion position as shown in FIG. 11A. Then the cell cover 64 is lifted together with the film retainer 61 by the rods 67 and the film transfer member 73 is inserted into the cell 42 through the opening 42a as shown in FIG. 11B. Then the Suction member 76 is moved upward and lifts the film 1 away from the film transfer member 73 as shown in FIG. 11C. When the suction member 76 lifts the film 1, it holds the film 1 under a suction force. After the film transfer member 73 is retracted away from the cell 42 as shown in FIG. 11D, the suction member 76 is moved downward so that the lower side of the film 1 abuts against the upper surface of the lower disk 45 of the incubator 12 as shown in FIG. 11E. Then the rods 67 are moved downward to permit the cell cover 64 and the film retainer 61 to move downward as shown in FIG. 11F. In this state, the film 1 is tightly enclosed in the cell cover 64 with the four corners thereof held down by the protrusions 61b of the film retainer 61. Then the suction member 76 is moved downward as shown in FIG. 11G.

Thus the film 1 is fixed in a predetermined position in the cell 42 and tightly enclosed by the cell cover 64. The light measuring window 59 is closed by the film 1 itself.

Coloring reaction (coloring matter forming reaction) is caused when the film 1 with the sample liquid is heated to a predetermined temperature in the cell 42 in the incubator 12, and the optical density of the coloring matter is measured by the light measuring head 95 after a predetermined time or at predetermined intervals.

Figure 12:
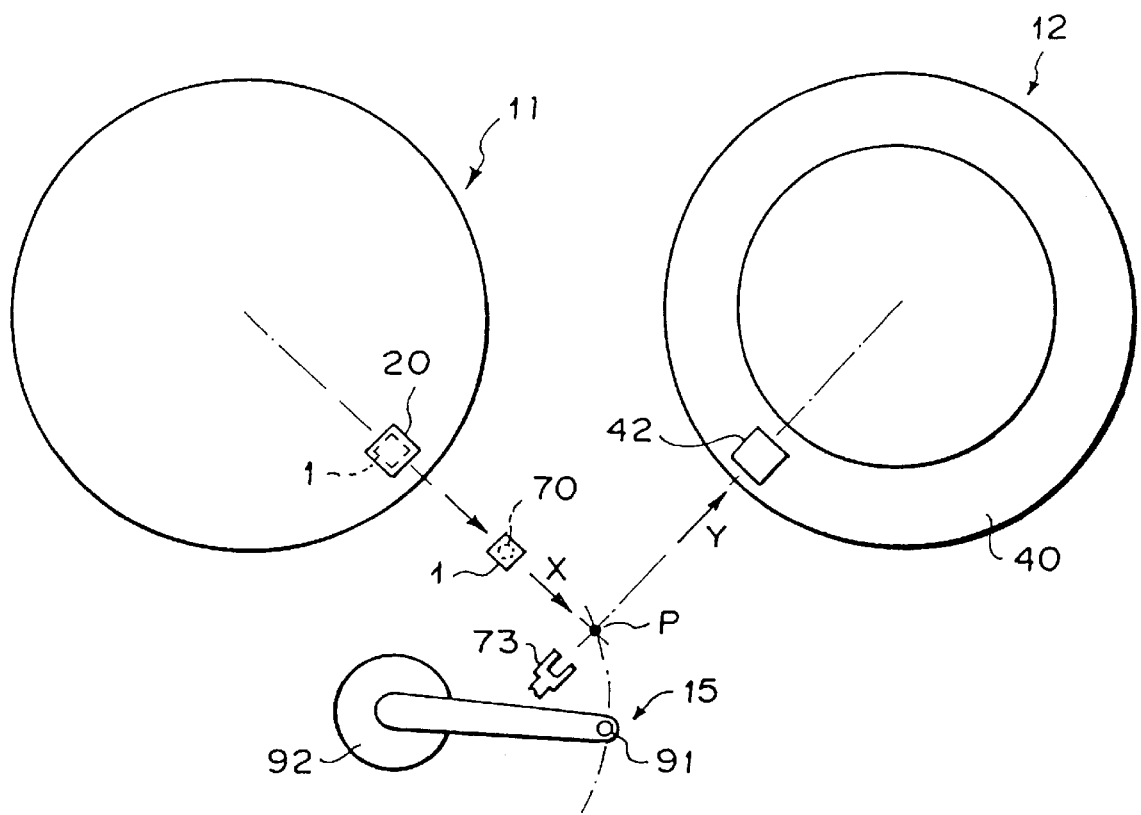
FIG. 12 is a view showing the path along which the frameless chemical analysis film is transferred to the incubator from the film supplier.

Referring to FIG. 12, the film 1 taken out from the cartridge 20 by the suction pad 70 is conveyed radially outwardly of the film supplier 11 in the first direction X and then transferred to the film transfer member 73 in the transfer position P. The film transfer member 73 conveys the film 1 toward the center of the incubator 12 in the second direction Y to insert the film 1 into the cell 42. The first and second directions X and Y are perpendicular to each other and the transfer position P is at the intersection of the first and second directions X and Y. The spotting means 15 spots the sample liquid at the transfer point P.

When the sample liquid spotted on the film 1 reaches a side of the reagent layer 1b, a part of the sample liquid can overflow and adheres to the side surface of the film 1 though does not drop. If the film 1 is brought into contact with the film retainer 61 or the like, the sample liquid will contaminate retainer 61. However, in this embodiment, since the film retainer 61 holds down the film 1 only at the four corners thereof where the sample liquid cannot reach and the other parts of the film retainer 61 are spaced from the film 1, the film retainer 61 cannot be contaminated with the sample liquid.

Further, the film transfer member 73 and suction member 76 are not brought into contact with the reagent layer 1b of the film 1 during transfer of the film 1, they cannot be contaminated with the sample liquid, whereby accuracy of the measurement can be ensured.

Further in the incubator 12 in the embodiment described above, since the metal disks 45 and 46 are directly heated by the heater 48, the films 1 are can be quickly heated and the preheating time can be shortened as compared with a system in which films 1 are heated on a disk positioned in a temperature-regurated chamber. Further the incubator 12 in the embodiment described above is advantageous over the latter system in that the chamber is not necessary, the thermal efficiency is high and a shutter for inserting the films 1 into the chamber can be eliminated, whereby the incubator can be simple in structure.

The cell covers 64 are arranged to be fit in the upper disk 46 and accordingly can be easily removed from the incubator 12 for cleaning or replacement. Further since the upper disk 46 can be easily removed from the incubator 12 by unscrewing the screws 47 and the upper surface of the lower disk 45 is flat, the upper surface of the lower disk 45 can be easily cleaned. Further the space in each cell 42 is closed by the cell cover 64 and the film 1, vapors and gases formed from the film 1 are prevented from flowing outside the cell 42. Since the film retainer 61 can be slid up and down, frameless chemical analysis films 1 having different thicknesses can be surely fixed by the film retainer 61.

Further since the engaging portions 64a of the cell cover 64 are formed on diagonally opposed corners of the lower portion of the cell cover 64, the space between the cell covers 64 can be smaller which results in miniaturization of the system, and at the same time the cell cover 64 can be lifted in a balanced position.

By continuing supplying suction force to the removing suction pad 81 after it lifts the film 1 and transfers it to the transfer member 82 during removal of the film 1 after measurement so that residual gas and/or air in the cell 42 and the vicinity thereof is sucked through the pad 81, the space in the cell 42 can be cleaned.

Though, in the embodiment described above, the present invention is applied to the biochemical analysis apparatus in which the concentration of a particular biochemical component is measured the change in the optical density due to chemical reaction between the particular biochemical component and the reagent layer, the present invention can be applied to other biochemical analysis apparatuses such as those in which the concentration of an electrolyte is measured through a difference in potential.

Though, in the embodiment described above, the first direction X in which the suction pad 70 is moved is directed to the center of the film supplier 11 and the second direction Y in which the film transfer member 73 is moved is directed to the center of the incubator 12, one or both of the directions X and Y may be deviated from the center of the corresponding member. Further, though, in the embodiment described above, the first and second directions X and Y are at right angles with each other, they may be at other angles so long as the film 1 can be rotated to conform to the second direction Y when it is transferred from the suction pad 70 to the film transfer member 73.

Figure 13:
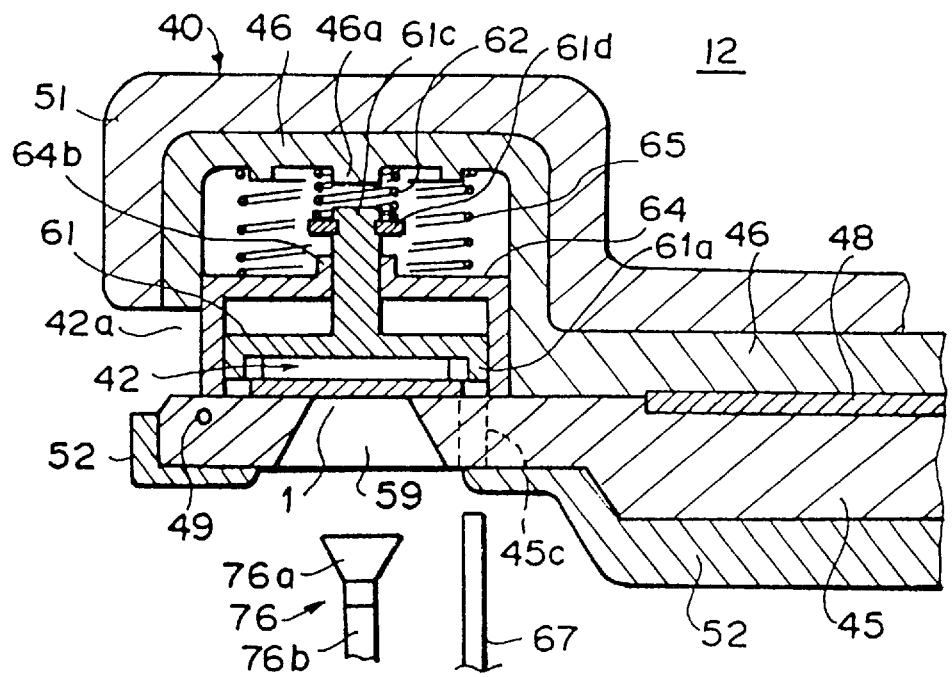
FIG. 13 is a view similar to FIG. 5 but showing a modification of the incubator.

FIG. 13 shows a modification of the incubator 12. Since the modification is substantially the same as that in the preceding embodiment, the parts analogous to those described in conjunction with the preceding embodiment are given the same reference numerals and only the difference of the modification from the incubator 12 in the preceding embodiment will be described hereinbelow.

As shown in FIG. 13, in this modification, the film retainer 61 has a rectangular frame portion 61a on the lower surface thereof. The inner dimensions of the frame portion 61a is larger than the outer dimensions of the frameless chemical analysis film 1 and a protrusion 61b is provided at each corner of the frame portion 61a to project inward. When the film retainer 61 is moved downward against the film 1, only the protrusions 61b are brought into contact with the film 1 so that the retainer 61 is not brought into contact with the portion S (FIG. 8) over which the sample liquid can spread. These features are the same as those described above in conjunction with FIGS. 6 and 8. The film retainer 61 has a shank portion 61c extending upward from the top of the retainer 61. A spring 62 for urging downward the film retainer 61 is compressed between the bottom of the channel in the upper disk 46 and a spring retainer 61d provided on the shaft portion 61d.

When the frameless chemical analysis film 1 is arranged so that the sample liquid spotted on the reagent layer 1b spreads laterally as shown in FIG. 8, the protrusions 61b may be arranged to hold down the upper and lower edges of the film 1.

Figure 14:
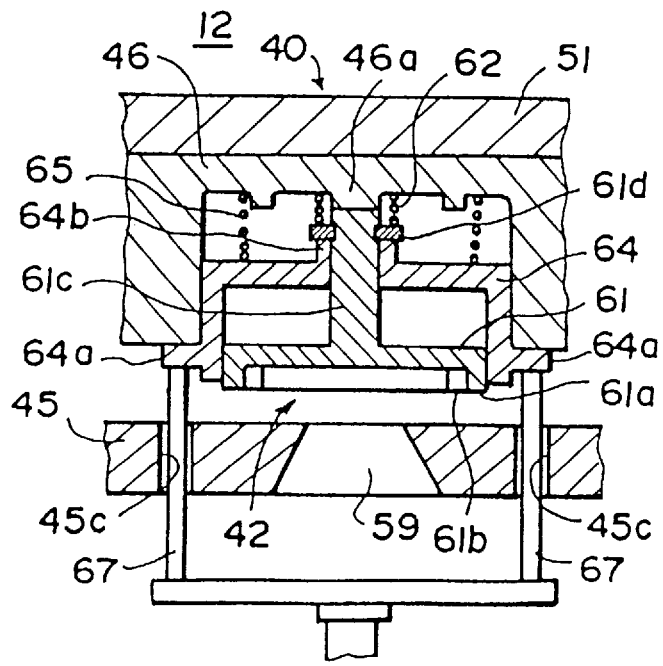
FIG. 14 is a view similar to FIG. 7 but showing the modification of the incubator.

The cell cover 64 has a box-like body portion open downward and is positioned to surround the film retainer 61. A guide portion 64b is formed in the top wall of the cell cover 64 and the shank portion 61c of the film retainer 61 is slidably fitted in the guide portion 64b to be guided by the guide portion 64b in up and down movements of the film retainer 61 relative to the cell cover 64. The cell cover 64 is received in the channel in the upper disk 46 for up and down movements and urged downward under the force of a spring 65 provided between the top wall of the cell cover 64 and the bottom of the channel in the upper disk 46. When the cell cover 64 is moved upward, the film retainer 61 is moved upward together with the cell cover 64 by way the engagement between the spring retainer 61d and the guide portion 64b as shown in FIG. 14. In this modification, since the spring 62 for urging downward the film retainer 61 is disposed outside the cell cover 64, the inner space of the cell cover 64 can be smaller in volume. When the cell cover 64 has a small inner space, vaporization of the sample liquid can be suppressed and the concentration of reaction gases can be made constant to stabilize the reaction. Further the internal surface area in contact with the reaction gasses becomes smaller and the amount of gas to be adsorbed by the wall of the cell cover 64 becomes smaller.

FIG. 15 shows another modification of the incubator 12. In this modification, the film retainer is formed integrally with the cell cover. That is, a cell cover 101 is slidably fitted in the channel of the upper disk 46 and is urged downward by a spring 103. The cell cover 101 abuts against the upper surface of the lower disk 45 at its lower end to form a sealed space for accommodating the frameless chemical analysis film 1. A film retainer 102 for holding down the four corners of the film 1 is integrally formed on the inner side of the top wall of the cell cover 101. The film retainer 102 is formed of a resilient material to be resiliently pressed against the film 1 when the cell cover 101 is pressed against the lower disk 45 under the force of the spring 103.

FIG. 16 shows still another modification of the incubator 12 where the film retainer is formed integrally with the cell cover.

A film retainer 105 similar to that shown in FIG. 13 is provided with protrusions 105a on the lower surface thereof at the respective corners to hold down the four corners of the film 1. A shank portion 105b extending upward from the center of the top wall of the film retainer 105 is slidably supported by a guide portion 108a formed in a upper disk 108. The amount of up and down movement of the film retainer 105 is limited by an abutment portion 105c. The film retainer 105 is urged downward under the force of a spring 107. A sealing member 106 formed of a flexible material extends downward from the film retainer 105 in a skirt-like fashion to surround the retainer 105. When the film retainer 105 is pressed against the upper surface of the lower disk 45 under the force of the spring 107, the protrusions 105a of the film retainer 105 hold down the film 1 and the lower edge portion of the sealing member 106 is pressed against the upper surface of the lower disk 45 to tightly enclose the film 1.

What is claimed is:

1. In a biochemical analysis apparatus in which a cartridge for storing a stack of a plurality of a dry-type frameless chemical analysis films each having a base and a reagent layer formed thereon is housed in a film supplier, and the dry-type frameless chemical analysis film is taken out from the cartridge, is spotted with a sample liquid and is transferred to an incubator to be incubated at a constant temperature, and the concentration of a biochemical component in the sample liquid is measured through a chemical reaction between the reagent layer and the biochemical component, the improvement comprising: a film takeout means which takes out the frameless chemical analysis film from the cartridge in the film supplier and conveys the film in a first direction and a film transfer means which receives the film from the film takeout means and conveys the film in a second direction into the incubator, the first and second directions being at an angle with respect to each other.

2. A biochemical analysis apparatus as defined in claim 1 in which the first and second directions are at right angles with each other.

3. A biochemical analysis apparatus as defined in claim 1 in which the sample liquid is spotted on the frameless chemical analysis film at the intersection or in the vicinity thereof, of the first and second directions.

4. A biochemical-analysis apparatus as defined in claim 1 in which the film takeout means comprises a suction member and the film transfer means comprises a horseshoe-shape film transfer member.

* * * * *